(12) United States Patent
Peng et al.

(10) Patent No.: US 8,512,459 B2
(45) Date of Patent: Aug. 20, 2013

(54) PRE-CONCENTRATION DEVICE AND METHOD FOR ION MOBILITY DETECTION APPARATUS

(75) Inventors: Hua Peng, Beijing (CN); Jin Lin, Beijing (CN); Liwei Song, Beijing (CN); Jun Lv, Beijing (CN); Yue Li, Beijing (CN)

(73) Assignee: Nuctech Company Limited, Beijing (CN)

( * ) Notice: Subject to any disclaimer, the term of this patent is extended or adjusted under 35 U.S.C. 154(b) by 0 days.

(21) Appl. No.: 12/999,600

(22) PCT Filed: Jun. 25, 2010

(86) PCT No.: PCT/CN2010/074524
§ 371 (c)(1),
(2), (4) Date: Dec. 16, 2010

(87) PCT Pub. No.: WO2011/075994
PCT Pub. Date: Jun. 30, 2011

(65) Prior Publication Data
US 2012/0247332 A1    Oct. 4, 2012

(30) Foreign Application Priority Data

Dec. 24, 2009    (CN) .......................... 2009 1 0243777

(51) Int. Cl.
*B01D 53/02*    (2006.01)
*B01D 53/06*    (2006.01)

(52) U.S. Cl.
USPC .................. 96/146; 96/143; 96/150; 95/107; 95/148; 55/354

(58) Field of Classification Search
CPC ................................................. G01N 1/2214
USPC ..................... 95/107, 148; 96/143, 146, 150, 96/153, 154; 55/354
See application file for complete search history.

(56) References Cited

U.S. PATENT DOCUMENTS 3,498,026 A * 3/1970 Daly et al. ...................... 95/107
3,797,200 A * 3/1974 Klass et al. ........................ 95/47
(Continued)

FOREIGN PATENT DOCUMENTS

| CN | 101611304 A | 12/2009 |
|---|---|---|
| CN | 102147340 A | 8/2011 |

(Continued)

OTHER PUBLICATIONS

International Search Report dated Oct. 28, 2010, for International Application No. PCT/CN2010/074524.

(Continued)

*Primary Examiner* — Robert Clemente
(74) *Attorney, Agent, or Firm* — Knobbe, Martens, Olson & Bear, LLP

(57) ABSTRACT

The present invention relates to a pre-concentration device and method for an ion mobility detection apparatus. According to an aspect of the invention, there is provided a pre-concentration device comprising: a collecting passage configured to collect a gas mixture including substances to be detected: a sieve provided, in a deploy state, within the collecting passage and configured to separate the substances from the gas mixture, the separated substances being absorbed to the sieve; at least one desorption unit configured to desorb the substances that have been absorbed to the sieve, the sieve being received in a wound state in the desorption unit; and a driving device configured to drive movement of the sieve between an absorption position in which the substances are absorbed to the sieve in the collecting passage, and a desorption position in which the substances are desorbed from the sieve in the at least one desorption unit.

15 Claims, 7 Drawing Sheets

(56) References Cited

U.S. PATENT DOCUMENTS

| | | | |
|---|---|---|---|
| 3,818,679 A * | 6/1974 | Klass et al. | 95/47 |
| 4,718,268 A | 1/1988 | Reid et al. | |
| 5,912,423 A * | 6/1999 | Doughty et al. | 95/107 |
| 6,085,601 A | 7/2000 | Linker et al. | |
| 6,345,545 B1 | 2/2002 | Linker et al. | |
| 8,012,231 B2 * | 9/2011 | Saitoh et al. | 55/486 |
| 2008/0121103 A1 | 5/2008 | Boyle et al. | |

FOREIGN PATENT DOCUMENTS

| | | |
|---|---|---|
| DE | 69030686 T2 | 9/1997 |
| DE | 69033217 T2 | 12/1999 |
| EP | 0447158 A2 | 9/1991 |
| GB | 2176008 A | 12/1986 |
| WO | WO 2007/113486 A1 | 10/2007 |

OTHER PUBLICATIONS

Written Opinion of International Search Report dated Sep. 21, 2010, for International Application No. PCT/CN2010/074524.

Chinese Office Action issued on Mar. 29, 2012 for Chinese Application No. 200910243777.X.

Office Action issued on Jul. 16, 2012 for German Patent Application No. 11 2010 000 036.0.

German Patent Office, issued on Jan. 15, 2013, for German Application No. 11 2010 000 036.0.

* cited by examiner

PRE-CONCENTRATION DEVICE AND METHOD FOR ION MOBILITY DETECTION APPARATUS

CROSS-REFERENCE TO RELATED APPLICATIONS

This application claims the benefit of PCT international application PCT/CN2010/074524, which was filed on Jun. 25, 2010 which claims priority of the Chinese application No. 200910243777.X filed on Dec. 24, 2009, and which is incorporated herein in its entirety by reference.

BACKGROUND OF THE INVENTION

1. Field of the Invention

The present invention pertains to the technical field of ion mobility detection application. Specifically, the present invention relates to pre-concentration technique for detecting drugs, explosives and other substances, which can be employed to pre-concentrate particles of drugs, explosives and other substances floating in air. More specifically, the present invention relates to a pre-concentration device and method for an ion mobility detection apparatus.

2. Description of the Related Art

In the prior arts, gas sample feeding methods used with an IMS instrument for detecting drugs, explosives and other substances primarily include the following two types. According to one type of analysis method, samples are continuously fed and sampled without gas pre-concentration processing. According to another type of the methods, separate gas pre-concentration processing and gas sampling are included.

However, in the analysis method comprising the separate gas pre-concentration processing and gas sampling, on one hand, it is required to provide a larger contact area when collecting substances, such as drugs and explosives, in the air so as to enhance adsorption abilities to absorb substances to be detected; on the other hand, it is required to obtain a higher substance volatilization concentration during detection to improve detection precision of the IMS (Ion Mobility Spectrometer) instrument. Unfortunately, providing a larger contact area during adsorption often causes the volatilization concentration of the substances to be lower during desorption. As a result, detection sensitivities of the IMS instrument are not high.

Further, the gas sampling step has to be implemented after the pre-concentration processing step has been implemented as the separate gas pre-concentration processing and gas sampling steps are employed, and the steps are repeated in this manner. Thus, detection efficiencies of the apparatus will be degraded.

SUMMARY OF THE INVENTION

In view of the above, this invention is made to overcome at least one aspect of the technical problems and defects existing in the prior arts.

Accordingly, an object of this invention is to provide a pre-concentration device and method for an ion mobility detection apparatus, which is capable of effectively improving detection sensitivities of the ion mobility apparatus.

Another object of this invention is to provide a pre-concentration device and method for an ion mobility detection apparatus, which is capable of effectively improve detection efficiencies of the ion mobility apparatus.

According to an aspect of this invention, a pre-concentration device for an ion mobility detection apparatus is provided. The pre-concentration device comprises: a collecting passage configured to collect a gas mixture including substances to be detected; a sieve provided, in a deploy state, within the collecting passage and configured to separate the substances to be detected from the gas mixture, and absorb the separated substances thereto; at least one desorption unit configured to desorb the substances to be detected that have been absorbed to the sieve, the sieve being received in a wound state in the desorption unit; and a driving device configured to drive the sieve to be movable between an absorption position in which the substances to be detected are absorbed to the sieve in the collecting passage, and a desorption position in which the substances to be detected are desorbed from the sieve in the at least one desorption unit.

Specifically, each desorption unit comprises: a sieve drum around/from which the sieve can be wound/unwound; and a heating barrel including a heating unit to heat the sieve received therein and wound on the sieve drum.

In a specific embodiment, the heating barrel comprises a barrel body with two open ends and a heating barrel cover connected to an end of the barrel body. The heating unit comprises an internal heating member and an external heating member connected to the heating barrel cover, wherein the internal heating member is provided inside of the sieve drum, and the external heating member is provided outside of the sieve drum.

Further, the pre-concentration device comprises a suction port provided in the heating barrel cover and communicated with an inner cavity of the heating barrel for guiding the separated substances to be detected from the sieve out of the heating barrel and into a sample feeding port of an IMS detection instrument.

Specifically, the sieve drum is in a hollow cage shape; and the sieve drum is inserted into the heating barrel through the other end of the barrel body of the heating barrel and is driven by the driving device to rotate in a forward direction and a reverse direction.

Preferably, the at least one desorption unit comprises first and second desorption units. The sieve has first and second adsorption regions spaced apart from each other along the longitudinal direction thereof, wherein the first adsorption region is moved into the first desorption unit for the desorption operation, and the second adsorption region is moved into the second desorption unit for the desorption operation.

Further, the driving device comprises: a driving motor; a plurality of synchronizing wheels, one of the plurality of synchronizing wheels being connected with the sieve drum via a synchronizing wheel connection shaft to drive the sieve drum to rotate; and a synchronizing belt configured to be connected with the plurality of synchronizing wheels and to be driven by the driving motor to rotate in the forward direction and the reverse direction.

More specifically, when one of the first and second adsorption regions is located at the adsorption position, the other one of the first and second adsorption regions is located at the desorption position.

In an embodiment, the pre-concentration device further comprises: first and second centrifugal blowers provided in the collecting passage to guide the gas mixture including the substances to be detected toward the first and second adsorption regions.

According to another aspect of this invention, a pre-concentration method for a gas mixture in an ion mobility detection apparatus is provided. The pre-concentration method comprises steps of:

(A) providing the pre-concentration device according to claim 1;

(B) guiding the gas mixture including the substances to be detected to the sieve in a deploy state for the adsorption operation at the first adsorption position;

(C) starting the driving device to drive the sieve into the desorption unit by winding the sieve for the desorption operation at the desorption position;

(D) after the desorption operation is completed, starting the driving device to return the sieve back to the absorption position.

Preferably, the pre-concentration method further comprises step (E) of: repeating steps of (B)-(D).

In a specific embodiment, the desorption operation comprises a step of heating the sieve that is received in the wound state in the desorption unit.

According to a further aspect of this invention, a pre-concentration method for a gas mixture in an ion mobility detection apparatus is provided. The pre-concentration method comprises steps of:

(a) providing the pre-concentration device according to claim 6 or 7;

(b) guiding the gas mixture including the substances to be detected to the first adsorption region of the sieve for the adsorption operation at the first adsorption position;

(c) starting the driving device to guide the first adsorption region of the sieve into the first desorption unit for the desorption operation at the first desorption position;

(d) guiding the gas mixture including the substances to be detected to the second adsorption region of the sieve for the adsorption operation at the second adsorption position while implementing step (c);

(e) after the desorption operation in the first adsorption region is completed, starting the driving device to guide the second adsorption region of the sieve into the second desorption unit for the desorption operation at the second desorption position; and (f) returning the first adsorption region of the sieve back to the first adsorption position while implementing step (e).

Preferably, the pre-concentration method further comprise step (g) of: repeating steps of (b)-(f) so that the whole process is circularly repeated.

The above exemplary embodiments of this invention have one or more aspects of the following advantages and effects:

1. During pre-concentration, the sieve is in a deploy state, so that a larger part of the area of the sieve can be used to adsorb substances, such as drugs and explosives, floating in the air. During detection, the sieve is in a wound state, and the substances adsorbed to the sieve volatilize in the small space by means of heating. In this way, concentration of the volatilized substances in the pre-concentration device can be improved, and it is more advantageous for the drugs and explosives detection instrument (IMS detection instrument) 3 to implement detection. This plays an important role for obtaining higher detection sensitivities.

2. The sieve is driven by the driving device to be automatically drawn back into the heating barrel, and is wound on the sieve drum or is drawn out of the heating barrel to be in a deploy state. Switch between the adsorption and desorption operations is automatically implemented by driving action of the driving device, so that detection efficiencies can be improved.

3. In a preferred embodiment, the device may employ two sets of heating barrels and drugs and explosives detection instruments (IMS instrument) and two desorption units, and the sieve may be provided with two adsorption regions. When two sets of heating barrels and drugs and explosives detection instruments (IMS) are employed, one set of the two sets is used for detection, while the other set of the two sets is in a standby state. When one of the first and second adsorption regions is located at the adsorption position, the other of the first and second adsorption regions is located at the desorption position. This process is circularly repeated by means of driving of driving mechanisms, thereby further improving detection efficiency.

BRIEF DESCRIPTION OF THE DRAWINGS

The pre-concentration device and method for the ion mobility detection apparatus according to the embodiments of this invention will be described in conjunction with the drawings, in which.

Figure 1:
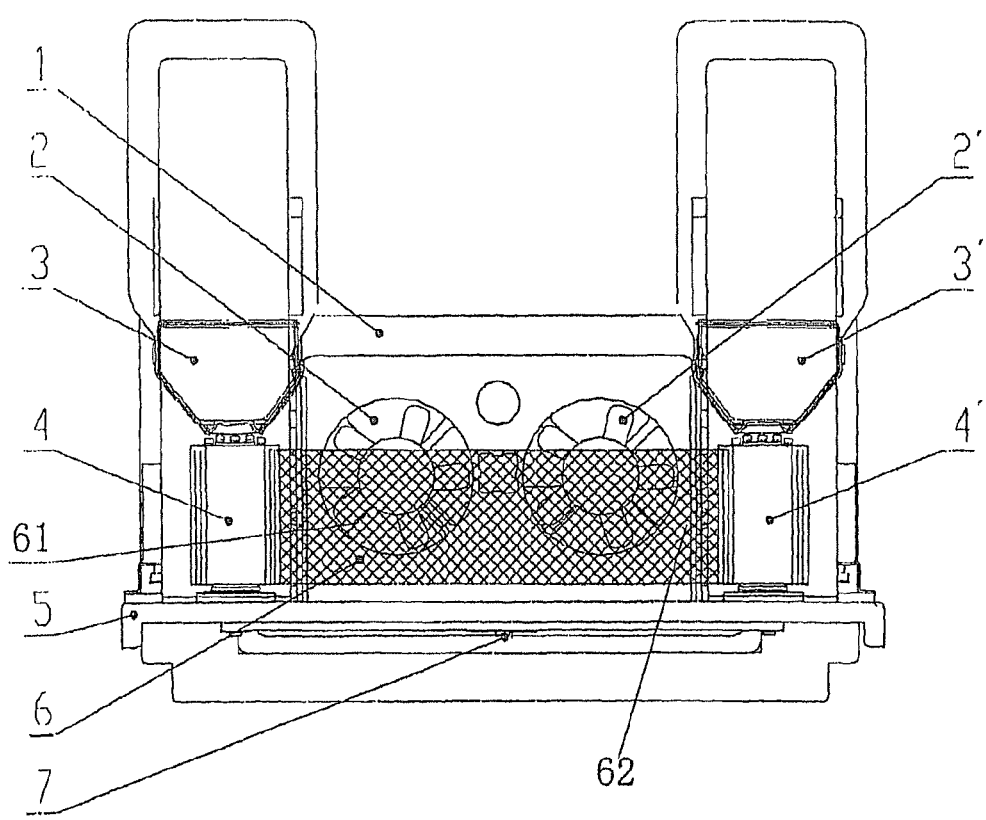
FIG. 1 is a front view of the pre-concentration device for the ion mobility detection apparatus according to an embodiment of this invention.

In the drawings, the components indicated by reference numbers are listed as follows: 1—collecting passage; 2—centrifugal blower or fan; 3, 3'—drugs and explosives detection instruments (IMS instrument); 4, 4'—heating barrels; 5—base; 6—sieve; 7—synchronizing wheel; 8—driving motor; 9—synchronizing belt; 10—suction port; 11—heating barrel cover; 12—internal heating member; 13—external heating member; 14—sieve drum; 15—synchronizing wheel connection shaft; 16—external heating block; 40—desorption unit; 60—driving unit; 61, 62—first and second adsorption regions; 101—inner cavity; 102—connection channel

DETAILED DESCRIPTION OF THE PREFERRED EMBODIMENT

The technical concept of this invention is explained in details with reference to embodiments in conjunction with the drawings. In the specification, the like reference numbers indicate the like components. The following description to the embodiments of this invention with reference to the drawings aims to explain the general inventive concept of this invention and is not intended to limit this invention.

With reference to FIGS. 1-6, a pre-concentration device for an ion mobility detection apparatus according to one preferred embodiment of this invention is shown. The pre-concentration device comprises a collecting passage 1 configured to collect a gas mixture including substances to be detected, a sieve 6 provided, in a deploy state, within the collecting passage 1 and configured to separate the substances to be detected from the gas mixture, the separated substances to be detected being absorbed to the sieve 6, at least one desorption unit 40 configured to desorb the substances that have been absorbed to the sieve 6, the sieve 6 being received in a winded state in the desorption unit 40, and a driving device 60 configured to drive movement of the sieve 6 between an absorption position in which the substances to be detected are absorbed to the sieve 6 in the collecting passage 1, and a desorption position in which the substances to be detected are desorbed from the sieve 6 in the at least one desorption unit 40.

Figure 2:
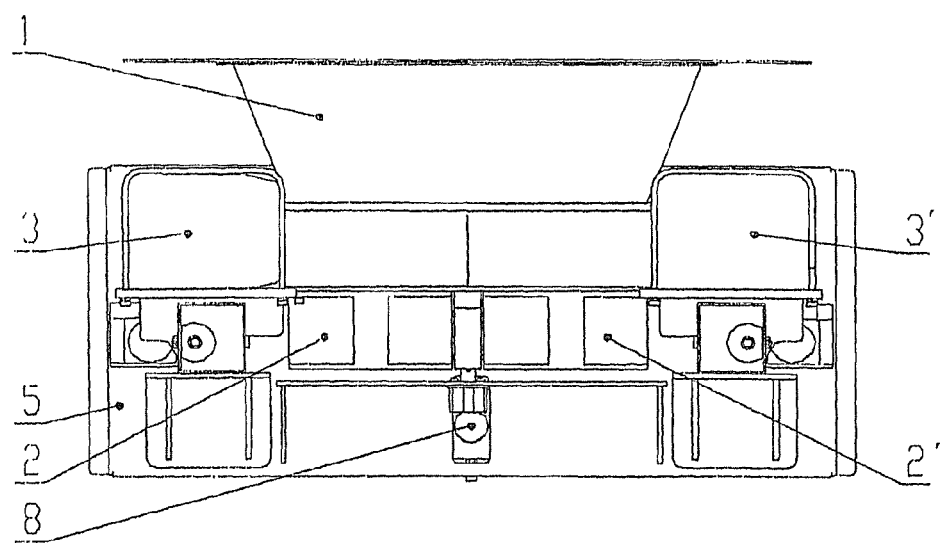
FIG. 2 is a top view of the pre-concentration device for the ion mobility detection apparatus.
Figure 5:
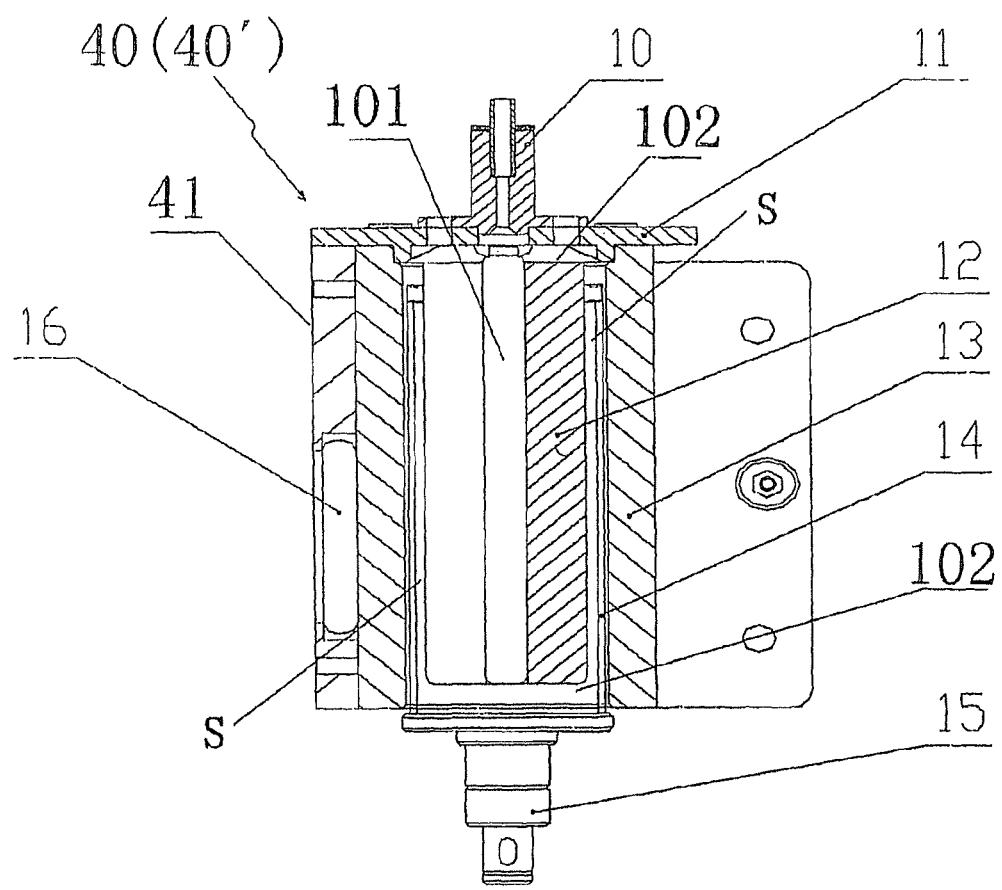
FIG. 5 is a cross-section view of the heating barrel of the pre-concentration device for the ion mobility detection apparatus.
Figure 6:
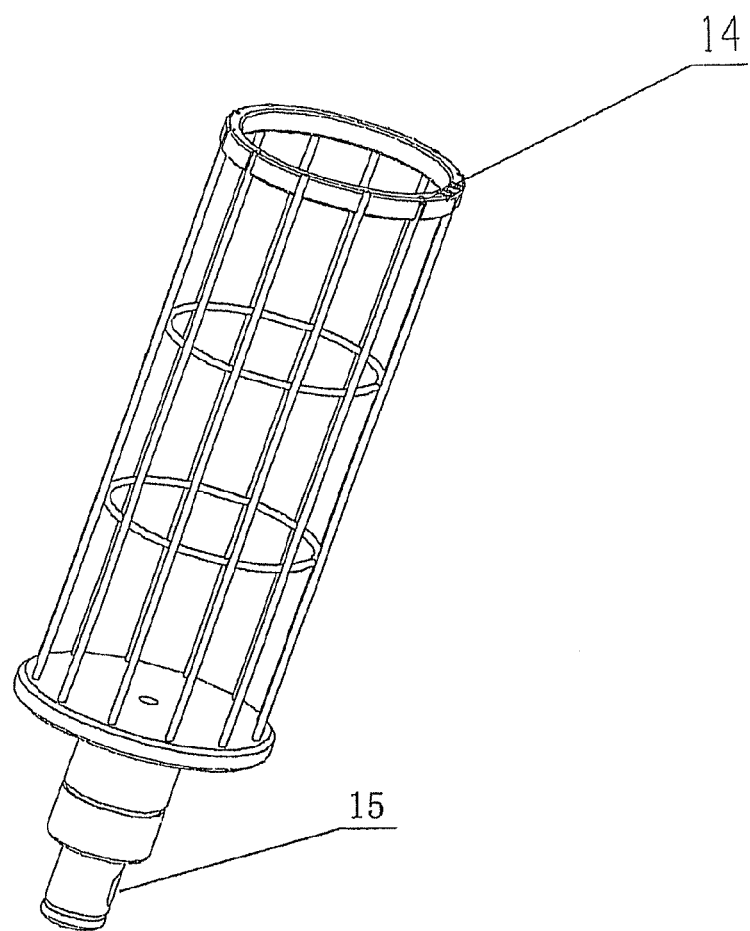
FIG. 6 is a perspective view of the sieve drum used in the pre-concentration device for the ion mobility detection apparatus.

Referring to FIG. 2, in the above embodiment, the collecting passage 1 may be communicated with a collecting passage (not shown) of a door-type human body security inspection system incorporated with an IMS instrument to guide the gas mixture including the separated substances to be detected from the human body, such as drugs, explosives and other suspicious particles, into the pre-concentration device. Referring to FIGS. 5 and 6, the desorption unit 40 comprises a sieve drum 14 around/from which the sieve 6 can be wound/unwound, and a heating barrel 4 including heating units 12 and 13 to heat the sieve 6 received therein and wound on the sieve drum 14.

Furthermore, as shown in FIG. 5, the heating barrel 4 comprises a barrel body 41 with two open ends and a heating barrel cover 11 connected to an end (the upper end shown in FIG. 5) of the barrel body 41. As shown in FIG. 6, the sieve drum 14 is in a hollow cage shape. The sieve drum 14 is inserted into the heating barrel 4 through another end (the lower end shown in FIG. 5) of the barrel body 41 of the heating barrel 4 and can be driven by the driving device 60 to rotate in a forward direction is and a reverse direction. With reference to FIG. 5, each of the heating units comprises an internal heating member 12 and an external heating member 13 connected to the heating barrel cover 11. The internal heating member 12 is provided inside of the sieve drum 14, and the external heating member 13 is provided outside of the sieve drum 14. With the above arrangement, during the desorption operation, the sieve wound around the sieve drum 14 is provided in a narrow space between the external heating member 13 and the internal heating member 12 to ensure that the desorption unit 40 can provide a higher volatilization concentration.

Various forms may be used for the external heating member 13 and the internal heating member 12, e.g. the form shown in FIG. 5 in which the external heating member 13 includes an external heating block 16 embedded into the main body thereof, such as a resistance heating block, an electromagnetic induction heating block, etc. In a modified embodiment, the external heating member 13 may be an external heating block 16 embedded into the barrel body 41 of the heating barrel 4. The external heating member 13 and the internal heating member 12 may be connected to the heating barrel 4, for example to the heating barrel cover 11 of the heating barrel 4, through various suitable ways, such as welding, riveting, and so on.

Furthermore, referring to FIG. 6, since the sieve drum 14 is in a hollow cage shape, the gas mixture including the substances to be detected, such as drugs, explosives and other suspicious particles, which are absorbed to the sieve drum 14, volatilizes to pass through the sieve drum 14 to enter into the narrow space S defined between the external heating member 13 and the internal heating member 12. As shown in FIG. 6, connection channels 102, communicated with an inner cavity 101 of the heating barrel 4, are provided at the upper end and the lower end of the space S to ensure that the volatilized substances to be detected can enter into the inner cavity 10, so that further detection can be implemented. As shown in FIG. 5, the pre-concentration device further comprises a suction port 10 provided in the heating barrel cover 11 and communicated with the inner cavity 101 of the heating barrel 4. The suction port 10 is used to guide the substances to be detected, separated from the sieve 6, out of the heating barrel 4 and into a sample feeding port (not shown) of the IMS detection instrument 3.

In the preferred embodiment shown in FIGS. 1-4, the pre-concentration device comprises first and second desorption units 40, 40'. The sieve 6 has first and second adsorption regions 61, 62 spaced apart from each other along the longitudinal direction thereof. The first adsorption region 61 is moved into the first desorption unit 40 for the desorption operation, and the second adsorption region 62 is moved into the second desorption unit 40' for the desorption operation. Further, referring to FIGS. 2, 3, and 5, the driving device 60 comprises a driving motor 8, a plurality of synchronizing wheels 7, one of which is connected with the sieve drum 14 via a synchronizing wheel connection shaft 15 to drive the sieve drum 14 to rotate, and a synchronizing belt 9. The synchronizing belt 9 is connected with the plurality of synchronizing wheels 7 and is driven by the driving motor 8 to rotate in the forward direction and the reverse direction. In this way, the sieve drum 14 is driven by the synchronizing wheel connection shaft 15 to rotate in the forward direction and the reverse direction. In turn, the sieve drum 14 drives the sieve 6 to reciprocate between the adsorption position and the desorption position, so that the detection efficiency is improved. Specifically, when one of the first and second adsorption regions 61, 62 is located at the adsorption position, the other one of the first and second adsorption regions 61, 62 is located at the desorption position.

With reference to FIG. 1, the pre-concentration device may further comprise first and second centrifugal blowers or fans 2, 2' which are provided in the collecting passage 1 to guide the gas mixture including the substances to be detected toward the first and second adsorption regions 61, 62. Corresponding to the arrangement with the two desorption units 40, 40', the first and second adsorption regions 61, 62, and the first and second centrifugal blowers 2, 2', the pre-concentration device may be mounted with two sets of heating drums and drugs and explosives detection instruments 3, 3' (IMS). When two sets of heating drums and drugs and explosives detection instruments 3, 3' are mounted, one set of detection instrument 3 is used for implementing detection, while the other set of detection instrument 3' is in a standby state.

Figure 3:
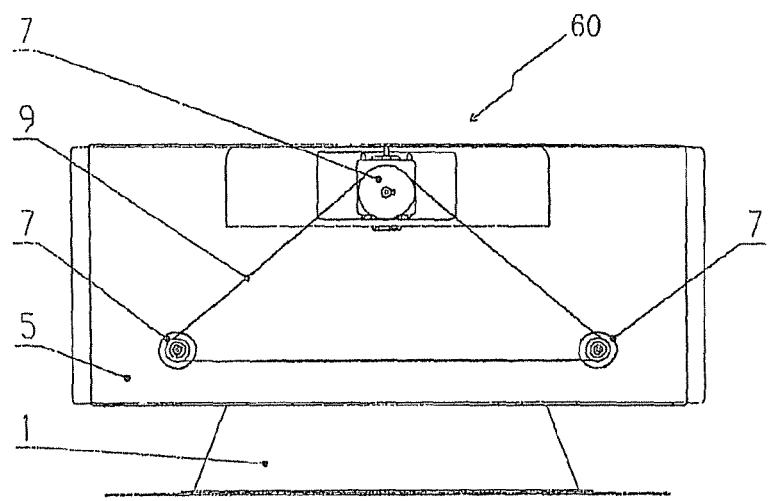
FIG. 3 is a bottom view of the pre-concentration device for the ion mobility detection apparatus.
Figure 4:
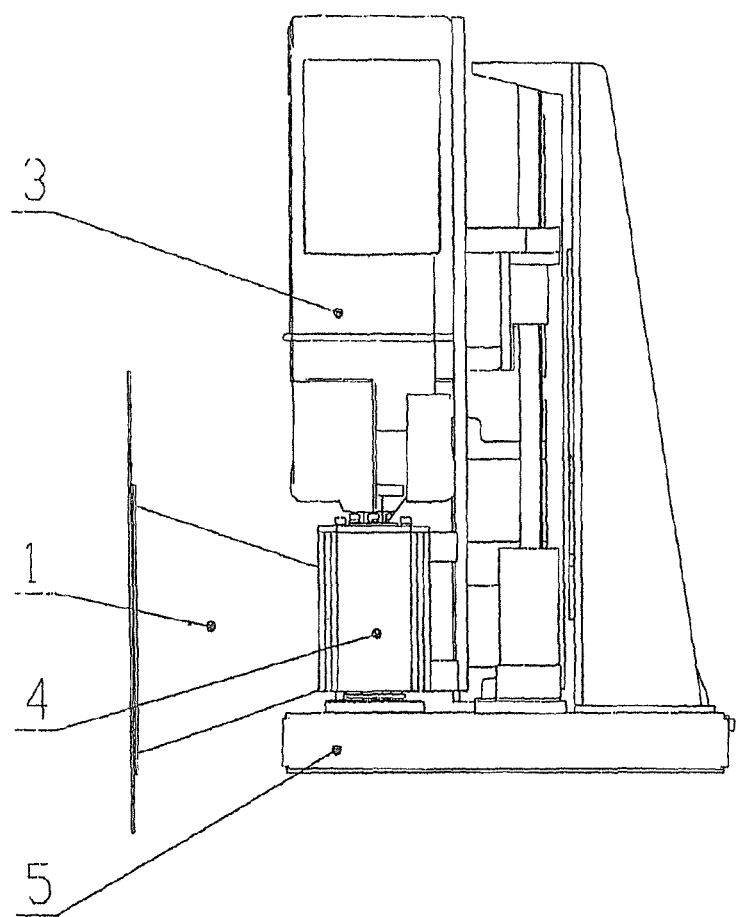
FIG. 4 is a left side view of the pre-concentration device for the ion mobility detection apparatus.

Referring to FIGS. 1-6 again, the heating drums 4, 4', the collecting passage 1 and the centrifugal blowers or fans 2, 2' all can be mounted on a base 5. As shown in FIGS. 2 and 3, the driving motor 8 (as the driving device 60), the synchronizing wheels 7, and the synchronizing belt 9 may be mounted within a lower space of the base. It is not limitative, but illustrative, although arrangements and positions of the respective components are described herein.

Figure 7:
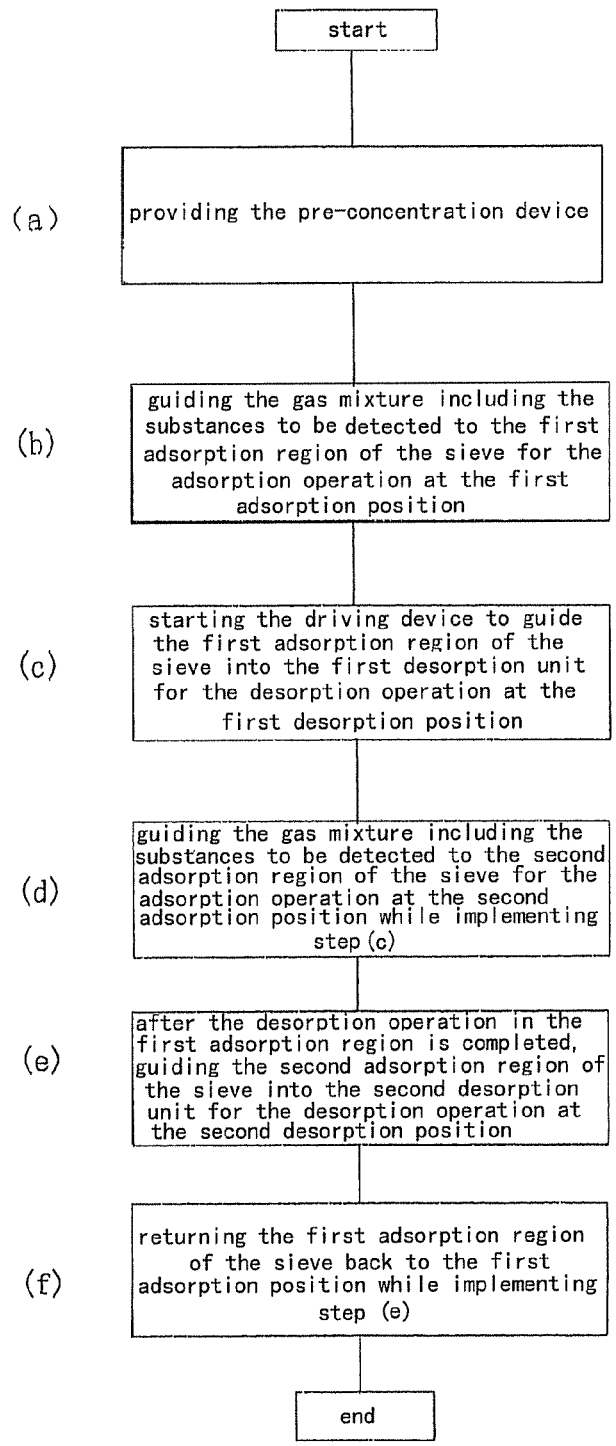
FIG. 7 is a flow chart of the pre-concentration method for the ion mobility detection apparatus according to an embodiment of this invention.

Next, the pre-concentration method of the gas mixture in the ion mobility detection apparatus according to the embodiment of this invention is described in conjunction with FIGS. 1-7. As shown in FIG. 7, the method comprises the steps of: providing the pre-concentration device as shown in FIGS. 1-6 (step a); guiding the gas mixture including the substances to be detected to the first adsorption region 61 of the sieve 6 for the adsorption operation at the first adsorption position (step b); starting the driving device 60 to guide the first adsorption region 61 of the sieve 6 into the first desorption unit 40 for the desorption operation at the first desorption position (step c); guiding the gas mixture including the substances to be detected to the second adsorption region 62 of the sieve 6 while implementing step (c) for the adsorption operation at the second adsorption position (step d); after the desorption operation in the first adsorption region 61 is completed, starting the driving device 60 to guide the second adsorption region 62 of the sieve into the second desorption unit 40' for the desorption operation at the second desorption position (step e); and returning the first adsorption region 61 of the sieve 6 back to the first adsorption position (step f).

Furthermore, steps (b)-(f) are repeated, so that the whole pre-concentration process is circularly repeated.

Specifically, after the system is ready, the centrifugal blower or fan 2 is started. The air flows through the collecting passage 1 and at the same time the first adsorption region 61 of the sieve 6 filters and adsorbs substances carried in the air that flows through the collecting passage 1. Since the sieve is provided, in a deploy manner, in the collecting passage 1 at that moment, it can be ensured that the sieve 6 sufficiently contacts with the gas mixture including the substances to be detected to provide advantages for improving detection sensitivities.

The centrifugal blower or fan 2 works for a period of time and then is stopped. Then, the driving motor 8 begins to work. The synchronizing wheels 7 and the synchronizing belt 9 are driven by the driving motor 8 to rotate. Winding of the first adsorption region 61 of the sieve 6 around the sieve drum 14 connected to the synchronizing wheel connection shaft 15 begins. When the first adsorption region 61 of the sieve 6 is being wound around the left-side heating drum 4, a portion of the sieve 6, i.e., the second adsorption region 62 of the sieve 6, is pulled out from the right-side heating drum 4. After the first adsorption region 61 of the sieve 6 is wound around the left-side heating drum 4, the internal heating member 12 and the external heating member 13 of the left-side heating drum 4 begin to heat the sieve 6. At this time, the substances adsorbed to the sieve 6 volatilize and enter into the inner cavity of the left-side heating drum 4. Since the sieve 6 is in a wound state during detection, and the substances adsorbed to the sieve 6 volatilize in the smaller space S by means of heating, concentration of the volatilized substances in the pre-concentration device is improved. In this way, it is more advantageous for the drugs and explosives detection instrument (IMS) 3 to implement detection. This plays an important role for obtaining higher detection sensitivities.

After the above desorption operation is completed, the left-side drugs and explosives detection instrument (IMS) 3 sucks the gas in the left-side heating drum 4 through the suction port 10 in the left-side heating drum 4 to implement detection. When desorption is implemented in the left-side heating drum 4 and/or the drugs and explosives detection instrument (IMS) 3 implements detection, the centrifugal blower or fan 2 starts, and again the second adsorption region 62 of the sieve 6 filters and adsorbs the substances carried in the air that passes through the collecting passage 1. After desorption operation in the left-side heating drum 4 and/or detection implemented by the drugs and explosives detection instrument (IMS) 3 are completed and the centrifugal blower or fan 2 stops, the driving motor 8 is started again to drive the synchronizing wheels 7 and the synchronizing belt 9 to rotate, and unwinding of the sieve 6 from the sieve drum 14 connected to the synchronizing wheel connection shaft 15 begins. A portion of the sieve 6, i.e., the first adsorption region 61 is pulled out from the left-side heating drum 4 while the second adsorption region 62 of the sieve 6 is wound around the right-side heating drum 4. After the sieve 6 is wound around the right-side heating drum 4, the internal heating member 12 and the external heating member 13 of the right-side heating drum 4 begin to heat the second adsorption region. At this time, the substances adsorbed to the second adsorption region 62 of the sieve 6 volatilize and enter to the inner cavity of the right-side heating drum 4. The right-side drugs and explosives detection instrument (IMS) 3 sucks the gas in the right-side heating drum 4 through the suction port 10 in the right-side heating drum 4 to implement detection.

By repeating the above steps, the above process is repeatedly operated, such that detection efficiencies are further improved.

Although the pre-concentration method of this invention is described with reference to the above preferred embodiment in which two sets of desorption units 40, 40' and drugs and explosives detection instruments (IMS) 3, 3' are employed, this invention is not limited thereto. When a single set of desorption unit 40, 40' and drugs and explosives detection instruments (IMS) 3, 3' is employed, the effect of pre-concentration also can be achieved.

Specifically, when only one desorption unit 4, one adsorption region 61, one centrifugal blower 2, and one set of heating drum and drugs and explosives detection instrument (IMS) 3 are employed (step A), the operation is as follows: guiding the gas mixture including the substances to be detected to the sieve 6 in a deploy state for the adsorption operation at the adsorption position (step B); starting the driving device 60 to guide the sieve 6 into the desorption unit 40 by means of winding the sieve 6 for the desorption operation at the desorption position (step C); after the desorption operation is completed, starting the driving device 60 to return the sieve 6 back to the adsorption position (step D). By repeating steps of (B)-(D), the above process can be repeatedly operated.

Although some embodiments of the general concept of the present invention have been shown and described, it would be appreciated by those skilled in the art that changes may be made in these embodiments without departing from the principles and spirit of the invention, the scope of which is defined in the claims and their equivalents.

What is claimed is:

1. A pre-concentration device for an ion mobility detection apparatus, comprising:
    a collecting passage configured to collect a gas mixture including substances to be detected;
    a sieve provided, in a deploy state, within the collecting passage and configured to separate the substances to be detected from the gas mixture, the separated substances to be detected being absorbed to the sieve;
    at least one desorption unit configured to desorb the substances that have been absorbed to the sieve, the sieve being received in a wound state in the desorption unit; and
    a driving device configured to drive the sieve to be movable between an absorption position in which the substances to be detected are absorbed to the sieve in the collecting passage, and a desorption position in which the substances to be detected are desorbed from the sieve in the at least one desorption unit;
    wherein each desorption unit comprises:
        a sieve drum around/from which the sieve can be wound/unwound; and
        a heating barrel including a heating unit to heat the sieve received therein and wound on the sieve drum;
        the heating barrel comprising a barrel body with two open ends and a heating barrel cover connected to an end of the barrel body; and
        the heating unit comprising an internal heating member and an external heating member connected to the heating barrel cover, wherein the internal heating member is provided inside of the sieve drum, and the external heating member is provided outside of the sieve drum.

2. The pre-concentration device according to claim 1, further comprising:
a suction port provided in the heating barrel cover and communicated with an inner cavity of the heating barrel for guiding the separated substances to be detected from the sieve out of the heating barrel and into a sample feeding port of an IMS detection instrument.

3. The pre-concentration device according to claim 1, where:
the sieve drum is in a hollow cage shape; and
the sieve drum is inserted into the heating barrel through the other end of the barrel body of the heating barrel and is driven by the driving device to rotate in a forward direction and a reverse direction.

4. The pre-concentration device according to claim 1, wherein:
the at least one desorption unit comprises first and second desorption units;
the sieve has first and second adsorption regions spaced apart from each other along the longitudinal direction thereof;
wherein the first adsorption region is moved into the first desorption unit for the desorption operation, and the second adsorption region is moved into the second desorption unit for the desorption operation.

5. The pre-concentration device according to claim 4, wherein the driving device comprises:
a driving motor;
a plurality of synchronizing wheels, one of the plurality of synchronizing wheels being connected with the sieve drum via a synchronizing wheel connection shaft to drive the sieve drum to rotate; and
a synchronizing belt configured to be connected with the plurality of synchronizing wheels and to be driven by the driving motor to rotate in the forward direction and the reverse direction.

6. The pre-concentration device according to claim 5, wherein:
when one of the first and second adsorption regions is located at the adsorption position, the other one of the first and second adsorption regions is located at the desorption position.

7. The pre-concentration device according to claim 6, further comprising:
first and second centrifugal blowers provided in the collecting passage to guide the gas mixture including the substances to be detected toward the first and second adsorption regions.

8. The pre-concentration device according to claim 2, wherein:
the at least one desorption unit comprises first and second desorption units;
the sieve has first and second adsorption regions spaced apart from each other along the longitudinal direction thereof;
wherein the first adsorption region is moved into the first desorption unit for the desorption operation, and the second adsorption region is moved into the second desorption unit for the desorption operation.

9. The pre-concentration device according to claim 3, wherein:
the at least one desorption unit comprises first and second desorption units;
the sieve has first and second adsorption regions spaced apart from each other along the longitudinal direction thereof;
wherein the first adsorption region is moved into the first desorption unit for the desorption operation, and the second adsorption region is moved into the second desorption unit for the desorption operation.

10. A pre-concentration method for a gas mixture in an ion mobility detection apparatus, comprising the steps of:
(A) providing the pre-concentration device according to claim 1;
(B) guiding the gas mixture including the substances to be detected to the sieve in a deploy state for the adsorption operation at the first adsorption position;
(C) starting the driving device to drive the sieve into the desorption unit by winding the sieve for the desorption operation at the desorption position;
(D) after the desorption operation is completed, starting the driving device to return the sieve back to the absorption position.

11. The pre-concentration method according to claim 10, further comprising step (E):
repeating steps of (B)-(D).

12. The pre-concentration method according to claim 10, wherein:
the desorption operation comprises a step of heating the sieve that is received in the wound state in the desorption unit.

13. A pre-concentration method for a gas mixture in an ion mobility detection apparatus, comprising the steps of:
(a) providing the pre-concentration device according to claim 4;
(b) guiding the gas mixture including the substances to be detected to the first adsorption region of the sieve for the adsorption operation at the first adsorption position;
(c) starting the driving device to guide the first adsorption region of the sieve into the first desorption unit for the desorption operation at the first desorption position;
(d) guiding the gas mixture including the substances to be detected to the second adsorption region of the sieve for the adsorption operation at the second adsorption position while implementing step (c);
(e) after the desorption operation in the first adsorption region is completed, starting the driving device to guide the second adsorption region of the sieve into the second desorption unit for the desorption operation at the second desorption position; and
(f) returning the first adsorption region of the sieve back to the first adsorption position while implementing step (c).

14. The pre-concentration method according to claim 13, wherein:
(g) repeating steps of (b)-(f).

15. The pre-concentration method according to claim 13, wherein:
the desorption operation comprises a step of heating the sieve that is received in the wound state in the desorption unit.

* * * * *